(12) United States Patent
Rosen

(10) Patent No.: US 6,844,156 B2
(45) Date of Patent: Jan. 18, 2005

(54) METHODS FOR IDENTIFYING A PREFERRED LIVER TRANSPLANT DONOR

(75) Inventor: Hugo R. Rosen, Tigard, OR (US)

(73) Assignee: The United States of America as represented by the Department of Veterans Affairs, Washington, DC (US)

(*) Notice: Subject to any disclaimer, the term of this patent is extended or adjusted under 35 U.S.C. 154(b) by 81 days.

(21) Appl. No.: 09/955,407

(22) Filed: Sep. 12, 2001

(65) Prior Publication Data

US 2002/0119468 A1 Aug. 29, 2002

Related U.S. Application Data

(63) Continuation of application No. 09/421,987, filed on Oct. 19, 1999, now abandoned.

(51) Int. Cl.[7] .............................. C12Q 1/68; A01N 1/00; C07H 21/04

(52) U.S. Cl. ........................... 435/6; 435/1.1; 536/24.31

(58) Field of Search ..................... 435/1.1, 6; 536/23.6, 536/24.31

(56) References Cited

PUBLICATIONS

Abrignani, "Bystander activation by cytokines of intrahepatic T cells in chronic viral hepatitis," *Semin. Liver Disease*, 17:319–322 (1997).
Arnold et al., "Soluble tumor necrosis factor receptors in patients with recurrent hepatitis C virus infection after liver transplantation," *Clin. Investig.*, 72:470 (1994).
Bernal et al., "Tumor Necrosis Factor Genomic Polymorphism and Outcome of Acetaminophen (Paracetamol)–induced Acute Liver Failure," *J. Hepatol.*, 29:53–59 (1998).
Booy et al., "Genetic influence on cytokine production in meningococcal disease," *Lancet*, 349:1176 (1997).
Boros et al., "Differential contribution of graft and recipient to perioperative TNF–α, IL–1β, IL–6 and IL–8 levels and correlation with early graft function in clincal liver transplantation," *Clin. Transplant.*, 11:588–592 (1997).
Cabrera et al., "Polymorphism in Tumor Necrosis Factor Genes Associated with Mucocutaneous Leishmaniasis," *J. Exp. Med.*, 182:1259–1264 (1995).
Colletti et al., "Role of Tumor Necrosis Factor–α in the Pathophysiologic Alterations after Hepatic Ischemia/Reperfusion Injury in the Rat," *J. Clin. Investig.*, 85:1936–1943 (1990).
Czaja et al., "Cytokine Polymorphisms Associated With Clinical Features and Treatment Outcome in Type 1 Autoimmune Hepatitis," *Gastoenterology*, 117:645–652 (1999).
Di Bisceglie, "Liver Transplantation for Hepatitis C: The Promise and the Challenge," *Hepatology*, 22:660–662 (1995).

DiMartino et al., "Longitudinal study of intrahepatic HCV replication after liver transplantation," *Hepatology*, 26:1343–1350 (1997).
Doughty et al., "Cholestatic hepatitis after liver transplantation is associated with persistently high serum hepatitis C virus RNA levels," *Liver Transplantation and Surgery*, 4:15–21 (1998).
Drouet et al., "Enhancers and Transcription Factors Controlling the Inducibility of the Tumor Necrosis Factor–α Promoter in Primary Macrophages," *J. Immunol.*, 147:1694–1700 (1991).
Eugster et al., "Multiple immune abnormalities in tumor necrosis factor and lymphotoxin–α double–deficient mice," *Int. Immunol.*, 8:23–28 (1996).
Folks et al., "Tumor necrosis factor α induces expression of human immunodeficiency virus in a chronically infected T–cell clone," *Proc. Natl. Acad. Sci. USA*, 86:2365–2368 (1989).
Freeman et al., "Tumor Necrosis Factor Genetic Polymorphisms Correlate With Infections After Liver Transplantation," *Transplantation*, 67:1005–1010 (1999).
Fukumoto et al., "Viral dynamics of hepatitis C early after liver transplantation: Evidence for rapid turnover of serum virions," *Hepatology*, 24:1351–1354 (1996).
Gane et al., "A longitudinal analysis of hepatitis C replication following liver transplantation," *Gastroenterology*, 110:167–177 (1996).
Grove et al., "Association of a Tumor Necrosis Factor Promoter Polymorphism With Susceptibility to Alcoholic Steatohepatitis," *Hepatology*, 26:143–146 (1997).
Gonzalez–Amaro et al., "Induction of Tumor Necrosis Factor α Production by Human Hepatocytes in Chronic Viral Hepatitis," *J. Exp. Med.*, 179:841–848 (1994).

(List continued on next page.)

*Primary Examiner*—Anne-Marie Falk
*Assistant Examiner*—Celine Qian
(74) *Attorney, Agent, or Firm*—Klarquist Sparkman, LLP

(57) ABSTRACT

The present invention provides a method of identifying a preferred liver transplant donor. The method includes the step of determining in an individual the presence or absence of a preferred genotype at a polymorphic site, where the preferred genotype is associated with altered activity of a tumor necrosis factor, and wherein the presence of the preferred genotype indicates that the individual is a preferred liver transplant donor. A preferred genotype can be associated with lower activity of a tumor necrosis factor such as TNF-α and can be, for example, TNF308.1. The methods of the invention are useful for identifying a preferred donor liver for transplant into a HCV infected patient. The invention additionally provides a method for selecting a preferred liver for transplantation. The invention further provides a method for limiting the recurrence of HCV infection in a liver transplant recipient.

6 Claims, 2 Drawing Sheets

OTHER PUBLICATIONS

Gretch et al., "Use of aminotransferase, hepatitis C antibody, and hepatitis C polymerase chain reaction RNA assays to establish the diagnosis of hepatitis C virus infection in a diagnostic virology laboratory," *J. Clin. Microbiol.,* 30:2145–2149 (1992).

Herrmann et al., "Polymorphisms of the tumor necrosis factor–α gene, coronary heart disease and obesity," *Eur. J. Clin. Invest.,* 28:59–66 (1998).

Höhler et al., "Tumor Necrosis Factor Alpha Promoter Polymorphism at Position –238 Is Associated With Chronic Active Hepatitis C Infection," *J. Med. Virol.,* 54:173–177 (1998).

Kamimura and Tsukamoto, "Cytokine gene expression by Kupffer cells in experimental alcoholic liver disease," *Hepatology,* 22:1304–1309 (1995).

Kaslow et al., "Influence of combinations of human major histocompatibility complex genes on the course of HIV–1 infection," *Nature Med.,* 2:405–411 (1996).

Larrea et al., "Tumor Necrosis Factor α Gene Expression and the Response to Interferon in Chronic Hepatitis C," *Hepatology,* 23:210–217 (1996).

Majno et al., "Mini–Review: Tumor Necrosis Factor (TNF) and TNF Soluble Receptors (TNF–sR) in Liver Disease and Liver Transplantation," *Swiss Surg.,* 1:182–185 (1995).

Marinos et al., "Tumor Necrosis Factor Receptors in Patients With Chronic Hepatitis B Virus Infection," *Gastroenterol.,* 108:1453–1463 (1995).

Messer et al, "Polymorphic Structure of the Tumor Necrosis Factor (TNF) Locus: An NcoI Polymorphism in the First Intron of the Human TNF–β Gene Correlates with A Variant Amino Acid in Position 26 and a Reduced Level of TNF–β Production," *J. Exp. Med.,* 173:209–219 (1991).

McGuire et al., "Variation in the TNF–α promoter region associated with susceptibility to cerebral malaria," *Nature,* 371:508–511 (1994).

Nedospasov et al., "DNA Sequence Polymorphism at the Human Tumor Necrosis Factor (TNF) Locus, Numerous TNF/Lymphotoxin Alleles Tagged by Two Closely Linked Microsatellites in the Upstream Region of the Lymphotoxin (TNF–β) Gene" *J. Immunol.,* 147:1053–1059 (1991).

Neumann et al., "Predictors of Sustained Response to Alpha Interferon Therapy in Chronic Hepatitis C," *Clin. Biochem.,* 32:537–545 (1999).

Pociot et al., "Functional Analysis of a New Polymorphism in the Human TNF α Gene Promoter," *Scand. J. Immunol.,* 42:501–504 (1995).

Rosen et al., "Use of OKT3 Is Associated with Early and Severe Recurrence of Hepatitis C after Liver Transplantation," *Am. J. Gastroenterol.,* 92:1453–1457 (1997).

Rosen et al., "Timing and severity of hepatitis C recurrence following liver transplantation as predictors of long–term allograft injury," *Transplantation,* 65:1178–1182 (1998).

Schluger et al., "Severe recurrent cholestatic hepatitis C following orthotopic liver transplantation," *Hepatology,* 23:971–976 (1996).

Stüber et al., "A genomic polymorphism within the tumor necrosis factor locus influence plasma tumor necrosis factor–α concentrations and outcome of patients with severe sepsis," *Crit. Care Med.,* 24:381–384 (1996).

Teramoto et al., "Expression of tumor necrosis factor–α gene during allograft rejection following rat liver transplantation," *Liver,* 19:19–24 (1999).

Warzocha et al., "Genetic Polymorphism in the Tumor Necrosis Factor Locus Influence Non–Hodgkin's Lymphoma Outcome," *Blood,* 91:3574–3581 (1998).

Webb and Chaplin, "Genetic Variability at the Human Tumor Necrosis Factor Loci," *J. Immunol.,* 145:1278–1285 (1990).

Wilson et al., "Effects of a polymorphism in the human tumor necrosis factor α promoter on transcriptional activation," *Proc. Natl. Acad. Sci. USA,* 94:3195–3199 (1997).

Wilson et al., "An Allelic Polymorphism within the Human Tumor Necrosis Factor α Promoter Region Is Strongly Associated with HLA A1, B8, and DR3 Alleles," *J. Exp. Med.,* 177:557–560 (1993).

Wilson et al., "Single base polymorphism in the human tumour necrosis factor alpha (TNFα) gene detectable by NcoI restriction of PCR product," *Hum. Mol. Genet.,* 1:353 (1992).

Wilson, "Genetics of tumor necrosis factor (TNF) in autoimmune liver disease: red hot or red herring?" *J. Hepatol.,* 30:331–333 (1999).

Zhou et al., "Severity of Liver Disease in Liver Transplantation Recipients With Hepatitis C Virus Infection: Relationship to Genotype and Level of Viremia," *Hepatology,* 24:1041–1046 (1996).

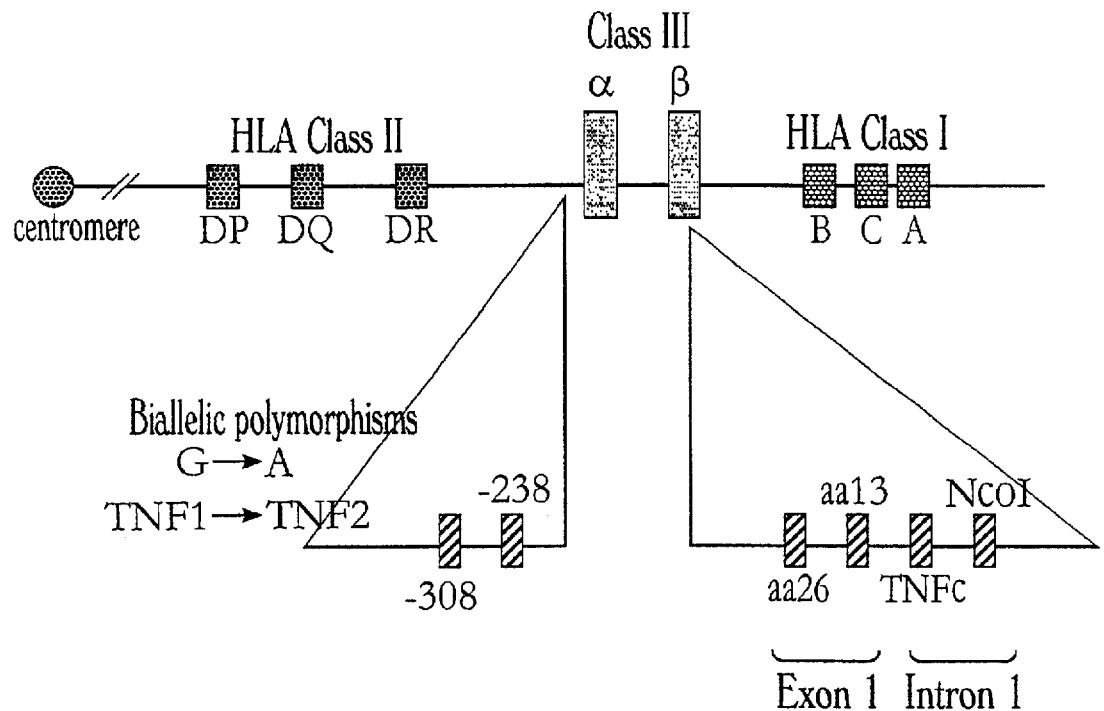
Fig. 1
Fig. 2
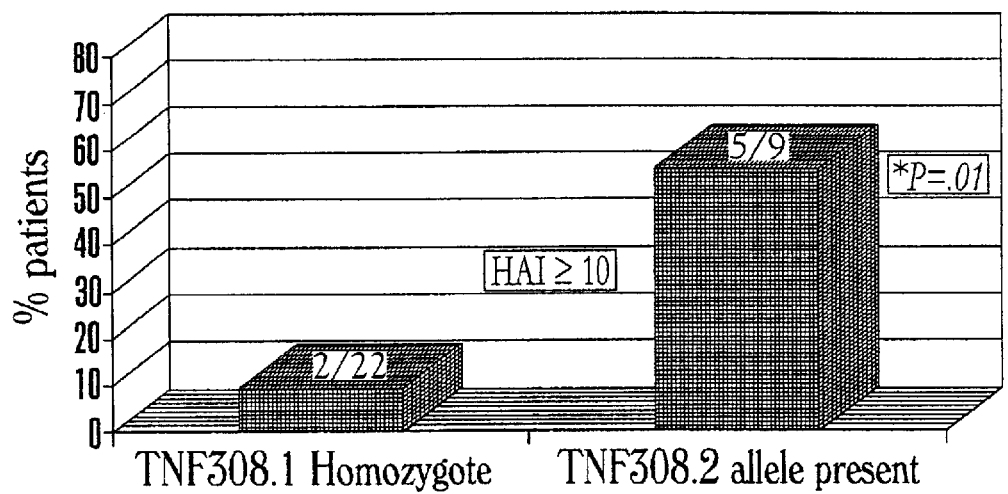

METHODS FOR IDENTIFYING A PREFERRED LIVER TRANSPLANT DONOR

This application is a continuation, of application Ser. No. 09/421,987, filed Oct. 19, 1999. Abandoned.

BACKGROUND OF THE INVENTION

The present invention relates generally to the field of molecular medicine and more specifically to methods of identifying a preferred liver transplant donor.

Chronic hepatitis C virus (HCV) infection afflicts an estimated 4 to 4.5 million Americans. HCV infection contributes to the deaths of more than 12,000 Americans every year and is a principal cause of chronic liver disease, cirrhosis, and liver cancer. Liver failure due to hepatitis C infection is the leading cause of liver transplants in the U.S.

Even though acute hepatitis C, at first, is largely asymptomatic, a flu-like illness is often mentioned by patients who are later diagnosed with the disease. About nine out of ten people who contract an acute infection of HCV will go on to develop chronic hepatitis, characterized by extreme fatigue, depression, fever, mood changes, and weakness. Of those who eventually develop chronic hepatitis C, a large number will develop cirrhosis, portal hypertension, and liver failure, some in as few as 10 years, and some will require a liver transplant. Hepatitis C is a silent killer because both the acute and chronic phases of the disease usually produce no specific symptoms. The acute phase is identified only if there is a definite recent risk factor such as a needle stick, surgery or a tattoo. Modes of transmission include body piercing, oral surgery, dialysis, acupuncture, vaccinations, and tainted blood products.

The chronic form of hepatitis C can persist for decades without any outward signs or symptoms of the disease while some patients are developing irreversible cirrhosis and possibly liver cancer. There is no cure or vaccine for hepatitis C, although a single treatment, alpha interferon, is available. Unfortunately, only about 15 percent of hepatitis C patients who take alpha interferon will go into remission.

During the next decade, the U.S. healthcare system could be overwhelmed by hepatitis C virus-related liver diseases, as deaths double and the need for liver transplants increase five-fold. The 20-year outlook is even more daunting, with HCV-related deaths projected to almost quadruple by 2018 and the demand for liver transplants expected to be eight times higher than today. It is estimated that the demand for orthotopic liver transplantation (OLT) will increase 5- to 7-fold in the next 10 to 20 years.

Unfortunately, following liver transplantation in a HCV infected patient, reinfection of the transplanted liver with HCV invariably occurs. Although an association between HCV infection and TNF-α expression has been previously described (Larrea et al., *Hepatology* 23:210–217 (1996)), no previous studies have investigated any possible contribution of the liver donor to TNF-α expression and the recurrence of hepatitis C in a liver transplant recipient. Because the rate, frequency and severity of hepatitis C recurrence after liver tranplantation varies with different patients, there exists a need to identify a preferred liver transplant donor whose transplanted liver would limit the severity of recurrence of hepatitis C. The present invention satisfies this need and provides related advantages as well.

SUMMARY OF THE INVENTION

The present invention provides a method of identifying a preferred liver transplant donor. The method includes the step of determining in an individual the presence or absence of a preferred genotype at a polymorphic site, where the preferred genotype is associated with altered activity of a tumor necrosis factor, and wherein the presence of the preferred genotype indicates that the individual is a preferred liver transplant donor. A preferred genotype can be associated with lower activity of a tumor necrosis factor such as TNF-α and can be, for example, TNF308.1. The methods of the invention are useful for identifying a preferred donor liver for transplant into a HCV infected patient.

The invention also provides a method for selecting a preferred liver for transplantation. The method includes the steps of obtaining material from one or more potential liver donors; determining in one or more potential liver donors the presence or absence of a preferred genotype at a polymorphic site, where the preferred genotype is associated with altered activity of a tumor necrosis factor; and harvesting a liver, or functional portion thereof, having a preferred genotype. The method can further include the step of transplanting the liver, or functional portion thereof, into a recipient.

The invention additionally provides a method for limiting the severity of recurrence of hepatitis C in a liver transplant recipient. The method includes the steps of obtaining material from one or more potential liver donors; determining in one or more potential liver donors the presence or absence of a preferred genotype at a polymorphic site, where the preferred genotype is associated with altered activity of a tumor necrosis factor; harvesting a liver, or functional portion thereof, having a preferred genotype; and transplanting the liver, or functional portion thereof, into a recipient infected with hepatitis C virus.

BRIEF DESCRIPTION OF THE DRAWINGS

FIG. 1 shows a physical map of the TNF locus, located between HLA class I and II on chromosome 6, and polymorphic sites in the TNF locus.

FIG. 2 shows the proportion of patients developing severe recurrence, as defined histologically by a total hepatic activity index (HAI)>10 on last follow-up allograft biopsy, according to whether the donor liver was homozygous for the TNF308.1 allele or heterozygote/homozygote for the TNF308.2 allele.

DETAILED DESCRIPTION OF THE INVENTION

Figure 3:
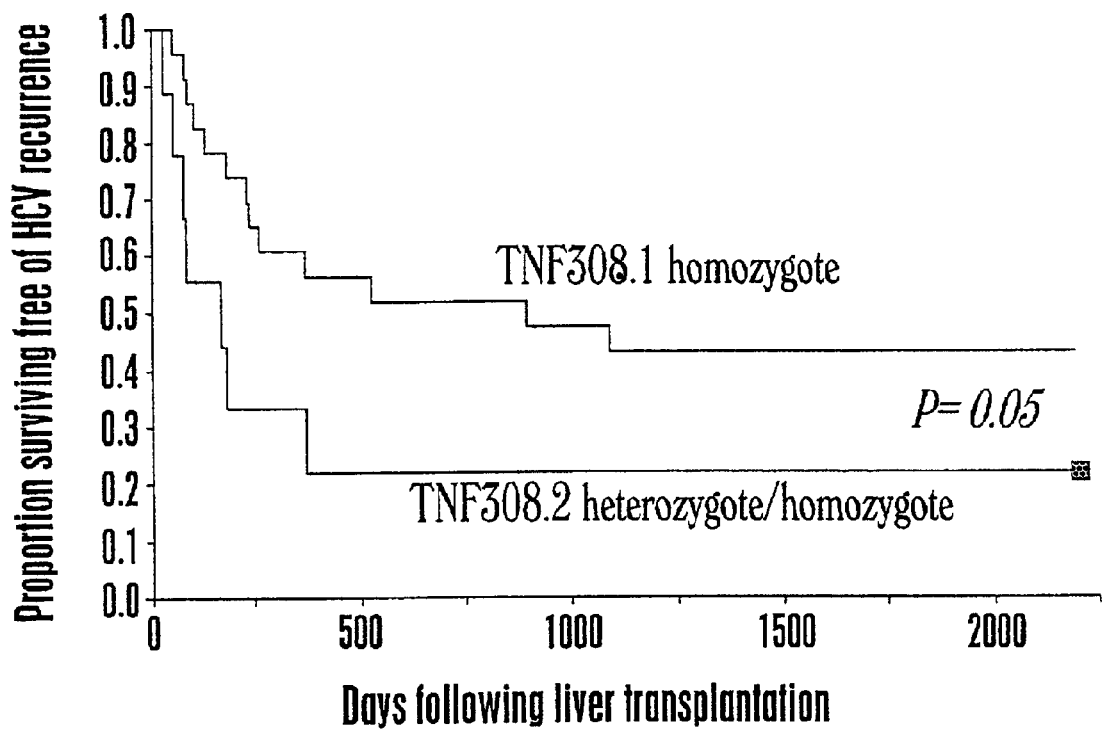
FIG. 3 shows the proportion of patients surviving free of hepatitis C recurrence (HCV recurrence). HCV recurrence-free survival, defined histologically, was significantly diminished in patients receiving a donor liver with a TNF308.2 allele (p=0.05, log-rank test).

The present invention provides a method of identifying a preferred liver transplant donor. The method of the invention includes the step of determining in an individual the presence or absence of a preferred genotype at a polymorphic site, where the preferred genotype is associated with altered activity of a tumor necrosis factor and wherein the presence of the preferred genotype indicates that the individual is a preferred liver transplant donor. The methods of the invention are directed to determining the genotype of a liver transplant donor to select a donor liver that provides an optimized patient outcome for the liver transplant recipient. The methods of the invention are particularly useful for identifying a preferred liver transplant donor for a patient having chronic hepatitis C.

As used herein, the term "polymorphic site" refers to a genetic site or locus having at least two different nucleotides occurring at that site in a population of the same organism. Thus, two or more alleles are found at the polymorphic site, each of which corresponds to a particular genotype.

As used herein, the term "preferred genotype," when used in reference to a potential liver transplant donor, means a genotype that increases the probability of a desirable patient outcome in a liver transplant recipient. A particular genotype is preferred if the genotype is more frequently associated with a desirable patient outcome for a liver transplant recipient than an alternate genotype. In a liver transplant recipient infected with HCV, the liver donor will become reinfected. However, the signs or symptoms associated with hepatitis C or HCV recurrence and can vary, and it is therefore desirable to have less severe recurrence such as less severe signs or symptoms associated with hepatitis C recurrence. As used herein, severe recurrence of hepatitis C generally refers to a hepatic activity index (HAI) greater than 10 and can be determined, for example, using histological criteria on a liver biopsy. For example, HCV disease severity can be defined by the modified Knodell hepatic activity index (HAI) with necroinflammatory subscores for piecemeal necrosis (0–4), confluent necrosis (0–6), focal lytic necrosis/apoptosis/focal inflammation (0–4), and portal inflammation (0–4), as well as fibrosis staging (0–6) (Ishak et al. *J. Hepatology* 22:696–699 (1995); see Example I). Therefore, a desirable outcome can be a HAI of 10 or less. In addition to milder recurrence, a desirable outcome can also be delayed onset of severe recurrence. A desirable outcome can also be prolonged survival or decreased allograft rejection. A desirable outcome can additionally be delayed recurrence of HCV infection. In some cases, a desirable outcome is exhibited by a transplant patient reinfected with HCV but having minimal signs or symptoms associated with severe hepatitis C recurrence.

As used herein, the term "preferred liver transplant donor" refers to a potential liver transplant donor having a preferred genotype. A preferred liver donor thus has a liver with a preferred genotype that predisposes a liver transplant recipient to a desirable outcome. For example, in the case of a HCV infected recipient, a desirable outcome includes milder recurrence or delayed recurrence, as described above.

As used herein, the term "altered activity," when used in reference to a cytokine such as tumor necrosis factor, refers to a change in the effective biological activity of the cytokine. A change in activity can be due to a change in the level of a cytokine so that the effective activity is increased or decreased with an increase or decrease in the amount of cytokine. A change in activity also can be due to a change in the amino acid sequence that alters the specific activity of the cytokine to increase or decrease its biological activity. Accordingly, the term "lower activity" encompasses both a "lower level" of a cytokine, corresponding to a decreased amount of the cytokine, or a cytokine having a mutation that results in a net decrease in biological activity, regardless of whether the amount of cytokine is the same or even increased.

An altered activity can be due to a genetic polymorphism that results in a genotype associated with the altered activity. The altered activity associated with a genotype is relative to an activity associated with an alternative genotype at that polymorphic site. For example, a polymorphism in a regulatory region can result in a change in the expression level of a polypeptide controlled by that regulatory region such that the amount of the polypeptide expressed is increased or-decreased. As used herein, the term "regulatory region" refers to a portion of a nucleic acid molecule that determines the expression of a polypeptide encoded by a corresponding gene. A regulatory region that controls transcription of a gene can be a promoter, the site of initiation of transcription, or an enhancer, a DNA sequence that increases the rate of transcription (Lewin, *Gene V*, Oxford University Press, New York (1994); Lodish et al., *Molecular Cell Biology*, 3rd ed., Scientific American Books, New York (1995)). Regulatory regions include 5', 3' and intronic regulatory regions. The transcriptional regulatory regions control the transcription rate of the gene. A regulatory region can also reside in the mRNA and regulate the translation of the mRNA, for example, by altering the stability or processing of the mRNA or by affecting the rate of translation. Thus, a regulatory region determines the expression of a polypeptide encoded by a gene by regulating the rate of transcription or translation.

A polymorphism can also occur in a coding region resulting in an amino acid change such as a missense or nonsense mutation that alters the biological activity of the encoded polypeptide. As used herein, the term "coding region" refers to the portion of the nucleotide sequence of the gene that encodes the gene product. A change in amino acid sequence can alter the specific activity of the polypeptide to increase or decrease its biological activity.

The methods of the invention are directed to identifying a preferred liver transplant donor by determining the presence or absence of a preferred genotype associated with altered activity of a tumor necrosis factor in a potential liver donor. Multiple mechanisms are likely involved in determining the severity of histological injury due to hepatitis C recurrence following liver transplantation, and most studies have focused on the contribution of viral factors and immunosuppression (DiBisceglie et al., *Hepatology* 22:660–663 (1995); Rosen et al., *Am. J. Gastroenterol.* 92:1453–1456 (1997); Zhou et al., *Hepatology* 24:1041–1046 (1996)). No study to date, however, has examined the genetic contribution of the donor liver to the risk of hepatitis C recurrence in a HCV infected recipient.

Tumor necrosis factor-α (TNF-α) and TNF-β are potent, multifunctional immunomodulators and mediators in the antiviral inflammatory response (Eugaster et al., *Int. Immunol.* 8:23–28 (1996)). These cytokines have been implicated in a number of clinical and experimental liver disease models, including alcoholic hepatitis (Kamimura and Tsukamoto, *Hepatology* 21:1304–1307 (1995)), viral hepatitis B (Marinos et al., *Gastroenterology* 108:1453–1455 (1995)), and ischemic-preservation injury following liver transplantation (Coletti et al., *J. Clin. Invest.* 85:1936–1939 (1990)). Although its precise role in the pathogenesis of HCV infection has not been clearly defined, a recent study demonstrated enhanced expression of the TNF-α gene in patients with ongoing HCV replication who fail to respond to antiviral treatment (Larrea et al., *Hepatology* 23:210–217 (1996)).

Tumor necrosis factor (TNF) was originally identified as a cytotoxic agent produced by macrophages and was subsequently shown to exist in two forms, TNF-α and TNF-β. TNF-α is a 17 kDa protein produced by macrophages and other cells and is a key mediator of inflammation and response to injury or invasion by microbes, parasites or neoplasia (Tracey, in *The Cytokine Handbook*, 2nd ed., Thomson, ed., pp. 289–304, Academic Press, San Diego, 1994)). TNF-α induces various cytokines and growth factors, including interleukin-1 (IL-1), IL-6, IL-8, granulocyte-macrophage colony stimulating factor (GM-CSF), nerve growth factor (NGF), transforming growth factor-β (TGF-β) and platelet-derived growth factor (PDGF). Factors that suppress effects of TNF-α include TGF-β, IL-10, TNF-α binding proteins (TNF-α BPs) and ciliary neurotrophic factor (CNTF). Factors that enhance the effects of TNF-α include IL-1, interferon-γ (IFN-γ), lipopolysaccharide (LPS), and leukemia inhibitory factor (LIF). Factors that induce TNF-α include LPS, products of complement activation, TNF-α itself, IL-1, IL-2 and GM-CSF.

TNF-β, also known as lymphotoxin, is a 25 kDa protein produced by activated lymphocytes (Tracey et al., supra, 1994). TNF-β is a mediator of killing by cytolytic T cells, helper-killer T cells, natural killer (NK) cells, and lymphokine-activated killer (LAK) cells. The cytotoxic activity of TNF-β likely contributes to allograft rejection and graft-versus-host reactions as g well as some autoimmune diseases.

The genes encoding TNF-α and TNF-β are tandemly arranged within a 7-kb DNA locus in the class III region of the major histocompatibility complex, telomeric to the class II and centromeric to the class I region (Webb and Chaplin, *J. Immunol.* 145:1278–1285 (1990)). A number of polymorphic sites within the TNF genes have been identified, and specific mutations have been shown to correlate with increased or decreased constitutive and inducible expression (Wilson et al., *Proc. Natl. Acad. Sci. USA* 94:3195–3199 (1997); Messer et al.,*J. Exp. Med.* 25 173:209–219 (1991)). Biallelic polymorphisms within the TNF-α promoter region at nucleotide positions −238 and −308 result in two allelic forms in which the presence of guanine defines the common TNF1 (wild type) allele and the presence of adenine defines the uncommon TNF2 allele (Wilson et al., *Proc. Natl. Acad. Sci. USA* 94:3195–3199 1997)). Both TNF308.2 and TNF-β high producer alleles have been linked with the extended haplotype HLA A1-B8-DR3-DQ2 which has been associated with autoimmunity and rapid progression of HIV infection (Wilson et al., *J. Exp. Med.* 177:557–560 (1993); Kaslow et al., *Nature Med.* 2:405–408 (1996)).

One of the known TNF-α polymorphisms occurs at −238 in the TNF-α gene (see Example I). The common or "1" allele, denoted TNF238.1, has a "G" at position −238 of the TNF-α gene. The rare or "2" allele, denoted TNF238.2, has an "A" at position −238 of the TNF-α gene. The effect of the TNF238.2 allele on TNF-α production is unknown (Pociot et al., *Scand. J. Immunol.* 42:501–504 (1995)).

Another TNF-α polymorphism occurs at −308 of the TNF-α gene. The common or "1" allele, denoted TNF308.1, has a "G" at position −308 of the TNF-α gene. The rare or "2" allele, denoted TNF308.2, has an "A" at position −308 of the TNF-α gene. The TNF308.2 allele is associated with higher levels of TNF-α (Wilson, *J. Hepatology* 30:331–333 (1999)). The TNF308.2 allele appears to be a stronger transcriptional activator.

In addition to the polymorphic −238 and −308 loci, three other polymorphisms have been reported in the TNF-α gene at positions −857, −851 and +691 (Herrmann et al., *Eur. J. Clin. Invest.* 28:59–66 (1998)). The polymorphism at position −857 is a change from C to A. The polymorphism at position −851 is a change from C to T. The polymorphism at position +691 is a deletion of a G in a non-translated region of the TNF-α gene.

Known TNF-β polymorphic sites include the TNFc locus, the aa13 locus, the aa26 locus and the NcoI locus (see Example I). The common or "1" allele at the TNFc locus, denoted TNFc1, is characterized by a series of nine TC/GA dinucleotide sequence repeats. The rare or "2" allele, denoted TNFc2, is characterized by a series of ten TC/GA dinucleotide sequence repeats.

The aa13 polymorphism is present at amino acid 13 of the TNF-β leader sequence. The common or "1" aa13L allele has a "T" at position 207 of the TNF-β cDNA; the codon corresponding to the "1" allele encodes a cysteine. The rare or "2" aa13L allele has a "C" at position 207 of the TNF-β cDNA sequence; the codon corresponding to the "2" allele encodes an-arginine.

The aa26 polymorphism present at amino acid 26 of mature TNF-β has been previously described (Messer et al., *J. Exp. Med.* 173:209–219 (1991)). The common or "1" aa26 allele has a "C" at position 349 of the TNF-β nucleotide sequence; the codon corresponding to the "1" allele at aa26 encodes threonine. The rare or "2" aa26. allele has an "A" at position 349 of the TNF-β nucleotide sequence; the codon corresponding to the "2" allele encodes asparagine.

The NcoI restriction fragment length polymorphism in the first intron of TNF-β also has been previously described (Webb and Chaplin, *J. Immunol.* 145: 1278–1285 (1990)). Southern analysis has shown that a 10.5 kb NcoI fragment is most common, with a 5.4 TNF-β NcoI fragment present in a smaller number of individuals. The NcoI site is absent in the common or "1" allele, while the NcoI site is present in the rare or "2" allele.

In addition to known polymorphisms in TNF genes described above, polymorphisms in other cytokines or additional polymorphisms in TNF genes can be correlated with a desirable patient outcome in a liver transplant recipient and used in methods of the invention. One skilled in the art can readily determine if a preferred genotype at a polymorphic site is associated with a desirable patient outcome in a liver transplant recipient using well known methods, including the methods disclosed herein (see Example I). For example, a genotype at an identified polymorphic site can be correlated with a preferred liver transplant outcome by collecting a sufficient number of potential liver donors, determining the genotype in the potential liver donors, and correlating a genotype with a desirable patient outcome using statistical analysis (see Example I).

In addition to tumor necrosis factor, a preferred genotype can be associated with altered activity of other cytokines. As disclosed herein, a TNF-α genotype associated with decreased expression of TNF-α is a preferred genotype for a donor liver (see Example I). Therefore, genotypes of other cytokines that alter the activity or expression of TNF-α can be a preferred genotype. For example, as described above, cytokines induced by TNF-α include IL-1, IL-6 and IL-8, which mediate effects of TNF-α. Therefore, a genotype at a polymorphic site that is associated with a decrease in activity of IL-1, IL-6 and/or IL-8 can be a preferred genotype. Since decreased expression of TNF-α is a preferred phenotype for a donor liver, a genotype at a polymorphic site that increases activity of a cytokine or other factor that suppresses TNF-α, for example, TGF-β or IL-10, also can be a preferred genotype. Conversely, a genotype at a polymorphic site that decreases activity of a cytokine or other factor that enhances the effect of TNF-α, for example, TGF-β, IL-10 or CNTF, or that induces TNF-α expression, for example, IL-1, IL-2 or GM-CSF, can be a preferred genotype.

In addition to cytokines that affect TNF activity, a preferred genotype can be associated with other cytokines so long as the genotype is correlated with a desirable patient outcome in a liver transplant recipient. As described above, one skilled in the art can readily determine a correlation between a particular genotype and a desirable patient outcome. For example, excessive TNF-α production can be associated with more severe recurrence of hepatitis C due to an immunopathologic mechanism (see Example I). Therefore, a preferred genotype can be associated with a cytokine activity that suppresses an immunopathologic response. In such a case, a preferred genotype is associated with a decrease in activity that promotes an immunopathologic response or an increase in activity that suppresses an immunopathologic response.

Although an association between TNF-α expression in a liver transplant recipient and HCV infection has been previously described, no previous studies addressed the potential role of the liver donor in TNF-α expression or the effect of genetic polymorphisms in the liver donor on the recurrence of hepatitis C in a liver transplant recipient. As disclosed herein, a polymorphism at the −308 locus of the TNF-α gene was correlated with recurrence of hepatitis C in a liver transplant recipient (Example I). The TNF308.1 allele, which is a G at position −308, is associated with lower expression levels of TNFα. A second allele, TNF308.2, which is an A at position −308, is associated with higher expression of TNF-α (Wilson, *J. Hepatology* 30:331–333 (1999)). As disclosed herein, a donor liver having the TNF308.2 allele was correlated with a more rapid, frequent and severe recurrence of hepatitis C in a liver transplant recipient. In contrast, a donor liver having the TNF308.1 allele was correlated with a slower, less frequent and less severe recurrence of hepatitis C in a liver transplant recipient. Therefore, a potential liver transplant donor having the TNF308.1 genotype is a preferred donor liver for transplantation into a HCV infected patient.

The invention also provides methods for identifying a preferred liver transplant donor by determining the presence or absence of a preferred genotype, where the genotype is a preferred combination of specific alleles at two or more polymorphic sites. As described above and disclosed in Example I, one skilled in the art can readily determine a correlation between a particular genotype encompassing specific alleles at two or more polymorphic sites by determining a combination of specific alleles that correlate with a preferred patient outcome using statistical analysis. It is understood that any combination of alleles at two or more polymorphic sites can be a preferred genotype so long as the genotype is associated with a desirable patient outcome. Such a combination can be, for example, TNF308.1 with TNF328.1 or TNF238.2; TNF308.1 with aa13.1 or aa13.2 of TNF-β; TNF308.1 with aa26.1 or aa26.2 of TNF-β; or TNF308.1 with NcoI.1 or NcoI.2 alleles in TNF-β.

The invention also provides a method of identifying a preferred liver transplant donor by determining in an individual the presence or absence of a preferred genotype at a polymorphic site, where the preferred genotype is associated with a desirable outcome for the liver transplant recipient. A particular genotype can be associated with a desirable patient outcome even though the polymorphism does not have a direct effect on the biological activity or expression level of a gene associated with the polymorphic site. For example, a genotype at a polymorphic site in a coding region of a cytokine could have no measurable effect on the expression level or binding activity of the cytokine but could have a net effect on biological activity when combined with an altered genotype in the cytokine receptor resulting in an altered response and net change in activity of the cytokine. Therefore, a particular genotype at a polymorphic site need not be directly associated with a measurable change in activity of a polypeptide associated with the genotype so long as there is a correlation between the genotype and a preferred patient outcome.

The invention also provides a method for selecting a preferred liver for transplantation. The method of the invention includes the steps of obtaining material from one or more potential liver donors; determining in one or more potential liver donors the presence or absence of a preferred genotype at a polymorphic site, where the preferred genotype is associated with altered activity of a tumor necrosis factor; and harvesting a liver, or functional portion thereof, having a preferred genotype. The invention also provides a method further comprising the step of transplanting the liver, or functional portion thereof, into a recipient.

As used herein, the term "harvesting" when used in reference to a liver refers to the removal of an entire liver or removal of a functional portion of a liver that is sufficient to regenerate liver function in a liver transplant recipient. In general, a functional portion of a liver useful in the invention is at least about half of a functional liver.

One skilled in the art will know or can readily determine criteria indicating that an individual is a potential liver donor. For example, a potential liver donor will generally have no cancer indications, and there will be no evidence of sepsis or infection in the individual, for example, no infection with hepatitis A, B or C virus or human immunodeficiency virus (HIV).

In many cases, a potential liver donor is classified as brain dead. One skilled in the art will know or can readily determine the criteria for a brain dead individual that makes the individual suitable as an organ donor. For example, a brain dead individual will have no evidence of brain function. The lack of brain function can be documented with diagnostic methods such as EEG (electroencephalogram), in which certain patterns are associated with brain death. The lack of brain function can be further verified using other physical findings, including fixed and dilated pupils and lack of response to pain. Once a potential liver donor has been identified by these criteria, family consent is obtained, and the liver and any other organs are removed from the body.

In some cases, a potential liver donor is not brain dead but can donate a functional liver portion and survive. In such cases, a liver donor can generally donate up to about half of his or her liver and still survive.

The invention additionally provides a method for limiting the severity of recurrence of hepatitis C in a liver transplant recipient. The method of the invention includes the steps of obtaining material from one or more potential liver donors; determining in one or more potential liver donors the presence or absence of a preferred genotype at a polymorphic site, where the preferred genotype is associated with altered activity of a tumor necrosis factor; harvesting a liver, or functional portion thereof, having a preferred genotype; and transplanting the liver, or functional portion thereof, into a recipient infected with hepatitis C virus.

The methods of the invention are directed to identifying a preferred genotype associated with altered activity of a tumor necrosis factor in a potential liver donor and selecting a preferred liver donor based on the presence of the preferred genotype. HCV infection is the major causative factor for liver dysfunction requiring a liver transplant. In such cases, the recurrence of HCV infection in the transplanted liver inevitably occurs. Therefore, the methods of the invention are directed to limiting the recurrence of hepatitis C by identifying a donor liver having genotypic characteristics that inhibit or limit the severity of recurrence of hepatitis C. As used herein, the phrase "limiting the severity of recurrence of hepatitis C" means that the signs or symptoms associated with hepatitis C recurrence are milder than the signs or symptoms associated with severe recurrence. Limiting the severity of hepatitis C recurrence can include, for example, a slower recurrence of HCV infection, a slower recurrence of signs or symptoms associated with hepatitis C, including a HAI of 10 or less, longer survival and decreased allograft rejection, as described above. In some cases, a transplant recipient can be chronically infected with HCV and yet show minimal signs or symptoms of hepatitis C recurrence.

In some cases, due to a lack of suitable donors having a preferred genotype, a liver transplant recipient can require transplantation of a donor liver that is not a preferred genotype. However, the methods of the invention for determining the genotype of the liver donor can still be useful for indicating a need to use more aggressive anti-viral therapy or a therapy that decreases TNF-α expression.

The methods of the invention are directed to determining the genotype at a polymorphic site in a nucleic acid by obtaining material from a potential liver donor. The material can be any biological material of the potential liver donor that contains nucleic acid and can conveniently be blood or liver biopsy, or any other biological material containing nucleic acid that can be readily obtained from the potential liver donor. As used herein, the term "nucleic acid" means a polynucleotide such as deoxyribonucleic acid (DNA) or ribonucleic acid (RNA) and encompasses both single-stranded and double-stranded nucleic acid. Total genomic DNA is a particularly useful nucleic acid with which to practice a method of the invention. When detecting a polymorphism in a coding region, mRNA or cDNA are also useful.

Methods of detecting a preferred genotype are well known to those skilled in the art. As disclosed herein, polymerase chain reaction (PCR) can be used to detect a preferred genotype (see Example I). Oligonucleotide PCR primers that flank a known polymorphism can be used to amplify genomic DNA containing the polymorphism. The amplified genomic DNA can then be sequenced and a particular allele associated with the polymorphism can be determined. Methods for PCR amplifying and sequencing a nucleic acid molecule are well known to those skilled in the art (see, for example, Sambrook et al., *Molecular Cloning: A Laboratory Manual,* 2nd ed., Cold Spring Harbor Press, Plainview, N.Y. (1989); Ausubel et al., *Current Protocols in Molecular Biology* (Supplement 47), John Wiley & Sons, New York (1999); Dieffenbach and Dveksler, *PCR Primer: A Laboratory Manual,* Cold Spring Harbor Press (1995)).

Other methods for detecting the presence or absence of a preferred genotype includes, for example, electrophoretic analysis and restriction fragment length polymorphism (RFLP) analysis. Electrophoretic analysis, as used herein in reference to one or more nucleic acid molecules such as amplified fragments, means a process whereby charged molecules are moved through a stationary medium under the influence of an electric field. Electrophoretic migration separates nucleic acid molecules primarily on the basis of their charge, which is in proportion to their size. The term electrophoretic analysis includes analysis using both slab gel electrophoresis, such as agarose or polyacrylamide gel electrophoresis, and capillary electrophoresis. Capillary electrophoretic analysis is generally performed inside a small-diameter (50–100-µm) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variants thereof, are well known in the art, as described, for example, in Ausubel et al., *Current Protocols in Molecular Biology* Chapter 2 (Supplement 47) John Wiley & Sons, Inc. New York (1999).

Restriction fragment length polymorphism (RFLP) analysis also can be useful for determining the presence or absence of a preferred genotype (Jarcho et al., in *Current Protocols in Human Genetics,* Dracopoli et al., eds., pages 2.7.1–2.7.5, John Wiley & Sons, New York (1994); Innis et al.,(Ed.), *PCR Protocols,* San Diego: Academic Press, Inc. (1990)). As used herein, restriction fragment length polymorphism analysis means any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Sequence analysis, which is any manual or automated process by which the order of nucleotides in a nucleic acid is determined, also can be useful for determining the presence or absence of a preferred genotype. It is understood that the term sequence analysis encompasses chemical (Maxam-Gilbert) and dideoxy enzymatic (Sanger) sequencing as well as variations thereof. Thus, the term sequence analysis includes capillary array DNA sequencing, which relies on capillary electrophoresis and laser-induced fluorescence detection and can be performed using, for example, the MegaBACE 1000 or ABI 3700. Also encompassed by the term sequence analysis are thermal cycle sequencing (Sears et al., *Biotechniques* 13:626–633 (1992)); solid-phase sequencing (Zimmerman et al., *Methods Mol. Cell Biol.* 3:39–42 (1992)) and sequencing with mass spectrometry such as matrix-assisted laser desorption/ionization time-of-flight mass spectrometry MALDI-TOF MS (Fu et al., *Nature Biotech.* 16: 381–384 (1998)). The term sequence analysis also includes, for example, sequencing by hybridization (SBH), which relies on an array of all possible short oligonucleotides to identify a segment of sequences present in an unknown DNA (Chee et al., *Science* 274:61–614 (1996); Drmanac et al., *Science* 260:1649–1652 (1993); and Drmanac et al., *Nature Biotech.* 16:54–58 (1998)). One skilled in the art understands that these and additional variations are encompassed by the term sequence analysis as defined herein (see, in general, Ausubel et al., supra, Chapter 7 and supplement 47).

Other methods for detecting the presence or absence of a preferred genotype at a polymorphic site include allele-specific oligonucleotide (ASO) hybridization. Allele-specific oligonucleotide hybridization is based on the use of a labeled oligonucleotide probe having a sequence perfectly complementary, for example, to a polymorphic site. Under appropriate conditions, the allele-specific probe hybridizes to a nucleic acid containing the polymorphic site but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify an allele by using an allele-specific oligonucleotide primer that is perfectly complementary to the nucleotide sequence of the allele but which has one or more mismatches as compared to other alleles (Mullis et al. (Eds.), *The Polymerase Chain Reaction,* Birkhauser, Boston, (1994)). One skilled in the art understands that the one or more nucleotide mismatches that distinguish between the allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the alleles at the 3' end of the primer.

A heteroduplex mobility assay (HMA) is another well known assay that can be used to detect a preferred genotype according to a method of the invention. HMA is useful for detecting the presence of a polymorphic sequence since a DNA duplex carrying a mismatch has reduced mobility in a polyacrylamide gel compared to the mobility of a perfectly base-paired duplex (Delwart et al., *Science* 262:1257–1261 (1993); White et al., *Genomics* 12:301–306 (1992)).

The technique of single strand conformational polymorphism (SSCP) also can be used to detect the presence or absence of a preferred genotype (see Hayashi, *PCR Methods Applic.* 1:34–38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also can be used to detect a preferred genotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

In addition to using DGGE as described above, other methods to detect heteroduplexes include temperature gradient gel electrophoresis (TGGE), constant denaturant gel electrophoresis (CDGE), and base excision sequence scanning (BESS) (Gupta, *The Scientist* 13:25–28 (1999)). Other methods include oligonucleotide ligation assay (OLA) in which a PCR-amplified target is hybridized to two oligonucleotides, one tagged, for example, with biotin, and the other with a reporter molecule and then ligated with DNA ligase. If the tag and reporter oligonucleotides are ligated, the tagged molecule can be used to isolate the ligated oligonucleotide and the reporter molecule can be detected.

Other well-known approaches for determining the presence or absence of a preferred genotype include automated sequencing and RNAase mismatch techniques (Winter et al., *Proc. Natl. Acad. Sci.* 82:7575–7579 (1985)). In view of the above, one skilled in the art realizes that the methods of the invention for determining the genotype in an individual can be practiced using one of the well known assays described above, or another art-recognized assay for genotyping. Furthermore, one skilled in the art understands that individual alleles can be detected by any combination of molecular methods (see, in general, Birren et al. (Eds.) *Genome Analysis: A Laboratory Manual* Volume 1 (Analyzing DNA) New York, Cold Spring Harbor Laboratory Press (1997)).

The following example is intended to illustrate but not limit the present invention.

EXAMPLE I

Donor Polymorphism of the TNF-α Gene is Correlated with Hepatitis C Recurrence

This example describes a correlation between a TNF-α allele in a liver donor and recurrence of hepatitis C in a liver transplant recipient.

The study group consisted of 31 patients who underwent orthotopic liver transplantation between July 1989 and November 1994. These patients were selected from a larger group of HCV-seropositive liver transplant recipients because stored donor tissue specimens were available. Donor spleen tissue was stored whenever available; no donor or recipient criteria were used to select specimens for storage. HCV had been diagnosed by ELISA 2.0 (Abbott Laboratories; Chicago Ill.) and/or polymerase chain reaction (PCR) as described previously (DiBisceglie, *Hepatology* 22:660–663 (1995)).

Liver biopsies were obtained for each patient by protocol at 7, 14, and 365 days, as indicated by an elevation from the baseline liver function biochemistries, and following treatment for acute cellular rejection. HCV disease severity was defined by the modified Knodell hepatic activity index (HAI) with necroinflammatory subscores for piecemeal necrosis (0–4), confluent necrosis (0–6), focal lytic necrosis/apoptosis/focal inflammation (0–4), and portal inflammation (0–4), as well as fibrosis staging (0–6) (Ishak et al. *J. Hepatoloqy* 22:696–699 (1995)). An average of 5.4 allograft biopsies were performed per patient.

Genomic DNA was isolated from frozen spleen samples (15 to 66 mg) using a commercial extraction kit (Puregene DNA Isolation Kit#D50K; Gentra Systems, Inc.; Minneapolis Minn.). For TNF-α promoter genotyping, a sample of this DNA was amplified by PCR using primers TNF3431 (5'-TCAGAATGAAAGAAGAGGGCCT-3')(SEQ ID NO:1) and TNF4034 (5'-CATTCAACCAGCGGAAAACTTCCT-3')(SEQ ID NO:2). The amplified DNA was then sequenced using primers TNF3517 (5'-CCTGCTACCCGCACCCAGCCT-3')(SEQ ID NO:3) and/or TNF3966 (5'-CCCTGCACCTTCTGTCTCGGT-3')(SEQ ID NO:4) using an automated sequencer (ABI377, PE-Applied Biosystems; Norwalk Conn.) and the AmpliTaq FS sequencing kit provided by the manufacturer. The sequence configuration at the −238 and −308 positions of the TNF-α promoter (Genbank accession number M16441) was determined. At each position, the more common allele 1 has a G base whereas the uncommon allele 2 has an A base (Wilson et al., *Proc. Natl. Acad. Sci. USA* 94:3195–3199 (1997)). Heterozygosity at either position was recognized by the presence of dual G/A peaks at the locus with peak heights that were within 20% of each other on the ABI377 sequence tracing.

Genotyping of selected loci of the TNF-α and TNF-β coding regions was performed by PCR amplification and restriction digestion. TNF-β aa13 and aa26 genotyping was performed using mutagenic primers that introduce a restriction enzyme half-site into the PCR product such that the corresponding enzyme can be used to discriminate between the two alleles of the polymorphism: aa13 is tested with HhaI and aa26 is tested with AclI (Cabrera et al., *J. Exp. Med.* 182:1529–1564 (1995)). For TNF-β NcoI genotyping, primers were designed so that the product would conveniently run with other products (243 bp length)(Cabrera et al., supra, 1995) TNFc genotyping was performed as previously described (Nedospasov et al., *J. Immunol.* 147:1053–1059 (1991)).

One-way analysis of variance and the Mantel-Haenszel chi-square test were used for statistical comparison of means (±S.E.M.) and proportions between groups, respectively. A P value of less than 0.05 was considered significant. The Kaplan-Meier product-limit estimate was used for the univariate analysis of time-dependent events, i.e., time to histologic recurrence, with comparison between groups performed via the log-rank test. The JMP (SAS Institute Inc; Cary N.C.) statistical package was used.

The physical map of the TNF locus and the polymorphic sites analyzed in the current analysis are shown in FIG. 1. The distribution of TNF genotypes is shown in Tables 1 and 2.

TABLE 1

Genotype Distribution for TNF-α Promoter Variants at Position −308.

| −308 alleles | n % | total HAI | Rejection |
| --- | --- | --- | --- |
| 1,1 (G/G) | 22 (71%) | 3.1 ± 0.9 | 7 (31.8%) |
| 1,2 (G/A) | 8 (25.8%) | 9.6 ± 2.1 | 6 (75%) |
| 2,2 (A/A) | 1 (3.2%) | 8 | 0 (0%) |
| P value | | .002 | .11 |

Twenty-two of 31 (71%) of patients received a donor liver homozygous for the TNF1 (wild type) allele at position −308. The mean HAI, total score of necroinflammatory subscores and fibrosis grade, of the last follow-up allograft biopsy was significantly greater in the subset of patients who had received a donor liver with one or two TNF2 alleles (Table 1). Accordingly, the cumulative necroinflammatory subscore (excluding the fibrosis grade) was significantly greater in patients who received a donor liver with one or two 308.2 alleles: 7.25+1.54 vs. 2.9+0.75 for patients homozygous for the TNF308.1 allele, p=0.008. On last follow-up biopsy, a greater proportion of patients with the TNF2 genotype developed severe recurrence, as defined by a total HAI>10: 5 of 9 (56%) with a donor liver having at least one TNF308.2 allele versus 2 of 22 with a donor liver homozygous for the TNF308.1 allele (9%; p=0.01) (FIG. 2).

The interval to histologic recurrence was significantly shorter and severity of HCV allograft hepatitis was significantly greater in patients with one or two TNF308.2 alleles. As shown in FIG. 3, the interval to the onset of documented histologic recurrence (indicated as "HCV recurrence" in FIG. 3) was shorter, and the proportion of patients who developed recurrence was greater in the subgroup receiving a donor liver with a TNF308.2 allele. There was no association with the prevalence of acute cellular rejection and the presence of these TNF-α alleles (p=0.11). Moreover, only 1 (3.2%) patient received a donor liver with the rarer TNF2 allele at position −238 (heterozygote).

There was no correlation between the TNF-β alleles and time to recurrence, severity of recurrence or the prevalence of rejection (Table 2).

TABLE 2

Distribution of TNF-α Alleles, Mean HAI of Last Allograft Biopsy, and Number of Patients with Rejection

| TNF-β genotypes | n | HAI | rejection |
| --- | --- | --- | --- |
| aa13 | | | |
| (1,1) | 19 | 5.6 ± 1.4 | 8 |
| (1,2) | 11 | 3.9 ± 1.7 | 4 |
| (2,2) | 1 | 4 | 1 |
| aa26 | | | |
| (1,1) | 13 | 4.1 ± 1.5 | 6 |
| (1,2) | 15 | 6.4 ± 1.6 | 6 |
| (2,2) | 3 | 2 ± 1.2 | 1 |
| TNFc | | | |
| (1,1) | 18 | 5.35 ± 1.4 | 7 |
| (1,2) | 12 | 4.45 ± 1.7 | 5 |
| (2,2) | 1 | 4 | 1 |
| Ncol | | | |
| (1,1) | 14 | 3.8 ± 1.5 | 6 |
| (1,2) | 13 | 6.7 ± 1.8 | 6 |
| (2,2) | 4 | 3.5 ± 1.7 | 1 |
| P value | | NS | NS |

In these studies, TNF genetic polymorphisms were determined in donor livers, and it was found that the presence of the less common 308.2 allele in the TNF-α promoter correlated with a more rapid, frequent and severe recurrence of hepatitis C in the recipient of a liver allograft. Patients who received donor livers with an inherited propensity for increased TNF-α production developed earlier histologic evidence of hepatitis C recurrence. Therefore, upon examination of a repertoire of polymorphic class III genes, it was found that a donor liver with an inherited susceptibility to excessive TNF-α production constitutes a risk factor for early and more severe hepatitis C recurrence. Excessive TNF-α could lead to an immunopathologic response that is ineffective in controlling HCV, allowing hepatitis C recurrence to occur more rapidly. Prior to these studies, no studies had addressed the potential contribution of a donor liver to the production of TNF-α in a liver transplant recipient and the recurrence of hepatitis C.

These results demonstrate that a donor liver having the TNF308.2 allele results in more rapid, frequent and severe recurrence of hepatitis C in a liver transplant recipient. In contrast, a liver donor having the TNF308.1 allele is results in a slower, less frequent and less severe recurrence of hepatitis C in a liver transplant recipient. Therefore, a donor liver having a TNF308.1 genotype is a preferred donor liver for transplantation into a recipient infected with HCV.

All journal articles and references provided herein, in parenthesis or otherwise, are incorporated herein by reference.

Although the invention has been described with reference to the examples provided above, it should be understood that various modifications can be made without departing from the spirit of the invention. Accordingly, the invention is limited only by the claims.

I claim:

1. A method of identifying a preferred liver transplant donor, comprising determining in both alleles of an individual the presence or absence of a preferred genotype at a polymorphic site, wherein said preferred genotype is a guanine (G) at position −380 in a gene encoding tumor necrosis factor α (TNF-α) relative to the transcription start site, and measuring the activity of said TNF-α, wherein the presence of said preferred genotype is associated with a decrease in the activity of TNF-α and indicates that said individual is a preferred liver transplant donor.

2. A method for selecting a preferred liver for transplantation, comprising (a) determining in one or more potential liver donors the presence or absence of a preferred genotype at a polymorphic site, and measuring the activity of TNF-α, wherein said preferred genotype is a guanine (G) at position −380 relative to the transcription start site in both alleles in a gene encoding TNF-α; (b) harvesting a liver, or functional portion thereof, having the preferred genotype associated with decreased TNF-α activity; thereby selecting a preferred liver for transplantation.

3. A method of identifying a preferred liver transplant donor, comprising
   determining in an individual a presence or an absence of a preferred genotype at a polymorphic site, wherein said preferred genotype comprises a guanine (G) at position −380 relative to the transcription start site in both alleles in a tumor necrosis factor (TNF) α promoter,
   wherein the presence of said preferred genotype indicates that said individual is a preferred liver transplant donor.

4. A method for selecting a preferred liver for transplantation, comprising
   determining in one or more potential liver donors the presence or absence of a preferred genotype at a polymorphic site, wherein said preferred genotype comprises a guanine (G) at position −380 relative to the transcription start site in a tumor necrosis factor (TNF) α promoter; and
   harvesting a liver, or functional portion thereof, having said preferred genotype in both alleles;
   thereby selecting said preferred liver for transplantation.

5. The method of claim 2, further comprising the step of:
   (c) transplanting said liver, or functional portion thereof, into a recipient.

6. The method of claim 5, wherein said recipient is infected with hepatitis C virus.

* * * * *

SEQUENCE LISTING

<160> NUMBER OF SEQ ID NOS: 4

<210> SEQ ID NO 1

-continued

```
<211> LENGTH: 22
<212> TYPE: DNA
<213> ORGANISM: Artificial Sequence
<220> FEATURE:
<223> OTHER INFORMATION: primer

<400> SEQUENCE: 1
tcagaatgaa agaagagggc ct                                              22

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
cattcaacca gcggaaaact tcct                                            24

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
cctgctaccc gcacccagcc t                                               21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ccctgcacct tctgtctcgg t                                               21
```